United States Patent [19]

Bitha et al.

[11] Patent Number: 4,675,336

[45] Date of Patent: Jun. 23, 1987

[54] PLATINUM COMPLEXES OF AMINES WITH DIBASIC ACIDS

[75] Inventors: Panayota Bitha, Pomona; Ralph G. Child, Pearl River; Joseph J. Hlavka, Tuxedo; Yang-I Lin, Nanuet, all of N.Y.

[73] Assignee: American Cyanamid Company, Stamford, Conn.

[21] Appl. No.: 748,788

[22] Filed: Jun. 26, 1985

[51] Int. Cl.[4] .................. C07F 15/00; A01N 55/04; A61K 31/32
[52] U.S. Cl. ................................ 514/492; 556/137
[58] Field of Search .................. 556/137; 514/492

[56] References Cited

U.S. PATENT DOCUMENTS

| | | | |
|---|---|---|---|
| 4,169,846 | 10/1979 | Kidani et al. | 556/137 |
| 4,203,912 | 5/1980 | Hydes et al. | 556/137 |
| 4,225,529 | 9/1980 | Hydes et al. | 556/137 |
| 4,230,631 | 10/1980 | Hydes et al. | 556/137 |
| 4,250,189 | 2/1981 | Hydes et al. | 556/137 |

FOREIGN PATENT DOCUMENTS 0130482 9/1985 European Pat. Off.

Primary Examiner—Helen M. S. Sneed
Attorney, Agent, or Firm—Susan H. Rauch

[57] ABSTRACT

Novel organic compounds of the formula

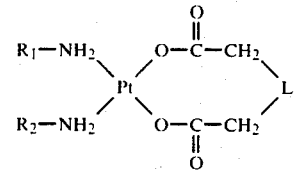

Where $R_1$ and $R_2$ are individually selected from the group consisting of hydrogen and alkyl($C_1$-$C_6$); or $R_1$ and $R_2$ taken together are selected from the group consisting of

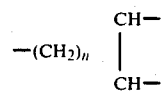

where n is an integer 3–6,

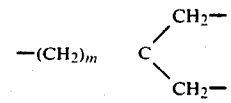

where m is an integer 3–6, and

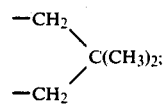

and L is selected from the group consisting of —O—, —CH$_2$—,

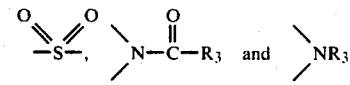

where $R_3$ is alkyl($C_1$-$C_6$) or —CH$_2$CH$_2$OH, which have antineoplastic activity, compositions containing the compounds and method of using the compounds to treat tumors in mammals.

17 Claims, No Drawings

PLATINUM COMPLEXES OF AMINES WITH DIBASIC ACIDS

SUMMARY OF THE INVENTION

This invention is concerned with new organic compounds of the formula

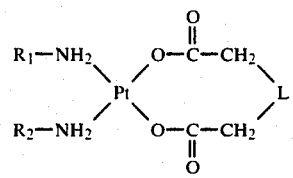

where $R_1$ and $R_2$ are individually selected from the group consisting of hydrogen and alkyl($C_1$-$C_6$); or $R_1$ and $R_2$ taken together are selected from the group consisting of

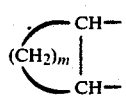

where n is an integer 3-6,

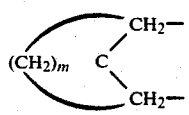

where m is an integer 3-6, and

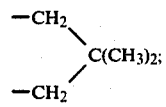

and L is selected from the group consisting of —O—, —CH$_2$—,

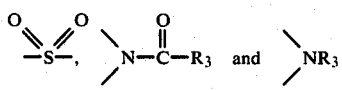

where $R_3$ is alkyl($C_1$-$C_6$) or CH$_2$CH$_2$OH. The novel compounds of the invention are advantageously used to induce palliation and/or regression of tumors in mammals.

DETAILED DESCRIPTION OF THE INVENTION

The compounds of this invention may be prepared according to the following flowchart and description:

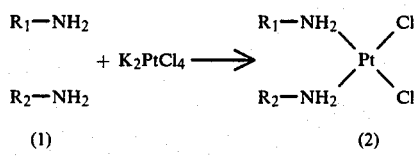

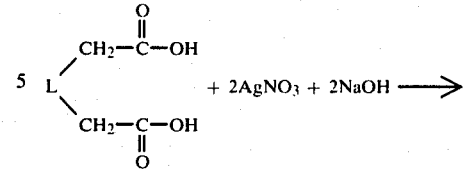

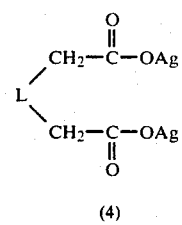

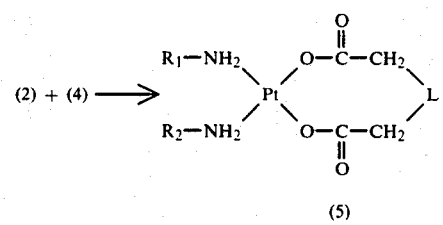

In accordance with the above flowchart an amine (1) where $R_1$ and $R_2$ are as described above is reacted with potassium tetrachloroplatinate in aqueous solution, giving the platinum chloride derivative (2).

A dicarboxylic acid (3) where L is as described above is reacted with sodium hydroxide and silver nitrate in aqueous solution giving the disilver salt (4). Reaction of (2) and (4) in aqueous solution provides the products (5).

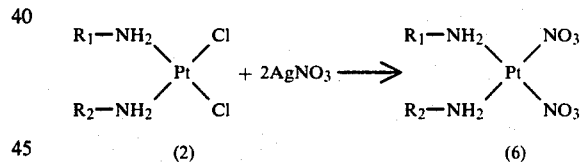

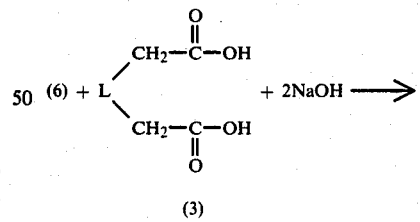

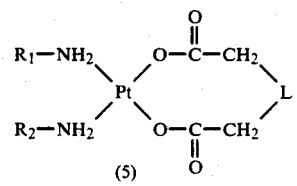

Alternatively, platinum derivative (2) may be reacted with silver nitrate in aqueous solution to give nitrate derivative (6) which is then reacted in aqueous solution with a dicarboxylic acid (3) and sodium hydroxide to give the products (5).

The novel compounds of this invention possess the property of inducing regression and/or inhibiting the growth of malignant neoplasms in mammals. This activity is demonstrated by the ability to increase the median survival time of mice transplanted with the following tumors: Lymphocytic Leukemia P388; Melanotic Melanoma B16; Lymphocytic Leukemia L1210; Colon 26 Adenocarcinoma; and M5076 Sarcoma. The National Cancer Institute customarily utilizes the first three of these assays in screening anticancer agents for potential clinical utility. In a study by the National Cancer Institute (reported by J. M. Venditti in "Pharmacological Basis of Cancer Chemotherapy", 1975, Williams & Williams Co.), it was concluded that activity against L1210, P388 and B16 melanoma transplanted in rodents would have predicted the clinical activity of most established anticancer drugs. The retrospective analysis of 45 clinically active drugs also indicated that the predictive value of activity against L1210 leukemia transplanted into mice extended to activity against human solid tumors as well as human leukemias and lymphomas. Nineteen of the 21 drugs active against human solid tumors met at least the minimal criteria of activity in the L1210 or P388 screens and thus would have been detected. Pertinent here also is the article by S. C. Silverstein, The Sciences, 1981, which further demonstrates the correlation between B16 mouse melanoma and melanoma in human beings.

In the following tests, the antitumor activity of representative novel compounds of the invention is also compared with the activity of Cisplatin, which is the only platinum antineoplastic agent currently on the market.

Lymphocytic Leukemia P388 Test

The animals used were BDF/1 mice, all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia $P_{388}$. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was Cisplatin. The results of this test with representative compounds of this invention appear in Table I.

TABLE I

| Lymphocytic Leukemia P388 Test | | | |
|---|---|---|---|
| Compound | Dose (mg/kg) | Median Survival (Days) | T/C × 100 (%) |
| trans-(racemic)-(1,2-cyclohexanediamine-N,N')[pentanedioato(2-)$0^1,0^5$]platinum | 100 | 21 | 191 |
| | 50 | 19 | 173 |
| | 25 | 19 | 173 |
| | 12.5 | 15.5 | 141 |
| | 6.2 | 15.5 | 141 |
| | 3.1 | 13 | 118 |
| Control | — | 11 | — |
| Cisplatin | 5 | 23 | 209 |
| | 2.5 | 28 | 255 |
| | 1.25 | 24 | 218 |
| (2,2-dimethyl-1,3-propanediamine-N,N')[[2,2'-oxybis-[acetato]]-(2-)$0^1,0^1$]platinum | 6.2 | 24.5 | 223 |
| | 3.1 | 23 | 209 |
| | 1.5 | 11.5 | 105 |
| | 0.8 | 12 | 109 |
| Control | — | 11 | — |
| Cisplatin | 1 | 16 | 145 |
| | 0.25 | 12 | 109 |
| trans-(racemic)-(1,2-cyclohexanediamine-N,N')[[2,2'-oxybis-[acetato]](2-)-$0^1,0^1$]-platinum | 6 | 13.5 | 112 |
| | 3 | 20.5 | 169 |
| Control | — | 12.1 | — |
| Cisplatin | 1 | 20.5 | 169 |
| | 0.25 | 17 | 141 |
| | 0.06 | 19 | 157 |
| Cis-(1,2-cyclohexanediamine-N,N') [[2,2'-oxybis[acetato]]-(2-)-$0^1,0^1$]platinum | 12.5 | 25 | 207 |
| | 6 | 22.5 | 186 |
| | 3 | 20 | 165 |
| Control | — | 12.1 | — |
| Cisplatin | 1 | 20.5 | 169 |
| | 0.25 | 17 | 141 |
| | 0.06 | 19 | 157 |
| diamine[[2,2'-oxybis[acetato]]-(2-)-$0^1,0^1$]platinum | 12 | 22 | 182 |
| | 6 | 19.5 | 161 |
| | 3 | 21 | 174 |
| Control | — | 12.1 | — |
| Cisplatin | 1 | 20.5 | 169 |
| | 0.25 | 17 | 141 |
| | 0.06 | 19 | 157 |
| (1,1-cyclopentanedimethanamine-N,N')[[2,2'-oxybis[acetato]]-(2-)-$0^1,0^1$]-platinum | 12.5 | 23.5 | 216 |
| | 6.2 | 18.5 | 170 |
| | 3.1 | 12 | 110 |
| | 1.6 | 11 | 101 |
| Control | — | 10.9 | — |
| Cisplatin | 1 | 20.5 | 188 |
| | 0.25 | 15 | 138 |
| bis (2-methylpropanamine)[[2,2'-oxybis[acetato]](2-)-$0^1,0^1$]-platinum | 50 | 20 | 165 |
| | 25 | 19 | 157 |
| | 12.5 | 18.5 | 153 |
| | 6.2 | 17.5 | 145 |
| | 3 | 18.5 | 153 |
| Control | — | 12.1 | — |
| Cisplatin | 1 | 21 | 174 |
| | 0.25 | 18 | 149 |
| trans-(-)-(1,2-cyclohexanediamine-N,N',)[2,2'-sulfonylbis-[acetato]](2-)-$0^1,0^1$]platinum | 12.5 | 24 | 235 |
| | 6.2 | 24 | 235 |
| | 3.1 | 20.5 | 201 |
| | 1.5 | 17 | 167 |
| | 0.8 | 14.5 | 142 |
| Control | — | 10.2 | — |
| Cisplatin | 1 | 18 | 176 |
| | 0.25 | 13.5 | 132 |
| (1,1-cyclobutanedimethanamine-N,N',)[[2,2'-oxybis[acetato]]-(2-)-$0^1,0^1$]platinum | 12.5 | 15 | 143 |
| | 6.2 | 21.5 | 205 |
| | 3.1 | 20 | 190 |
| | 1.5 | 18 | 171 |
| | 0.8 | 13.5 | 129 |
| | 0.4 | 11.5 | 110 |
| Control | — | 10.5 | — |
| Cisplatin | 1 | 22 | 210 |
| | 0.25 | 18 | 171 |
| | 0.06 | 14 | 133 |
| (1,1-Cyclohexanedimethanamine-N,N')[[2,2'oxybis[acetato]](2-)-$0^1,0^1$]platinum | 12.5 | 14 | 127 |
| | 6.2 | 27 | 245 |
| | 3.1 | 21 | 191 |
| | 1.5 | 15 | 136 |
| | 0.8 | 12 | 109 |
| Control | — | 11 | — |
| Cisplatin | 1 | 16 | 145 |
| | 0.25 | 12 | 109 |
| diammine[[2,2'-sulfonylbis-[acetato]](2-)-$0^1,0^1$]platinum | 25 | 22 | 183 |
| | 12.5 | 15.5 | 129 |
| | 6.2 | 13 | 108 |
| | 3.1 | 13 | 108 |
| Control | — | 12 | — |
| Cisplatin | 2.5 | 16 | 133 |
| | 1.25 | 20.5 | 171 |
| trans-(racemic)-(1,2-cyclohexanediamine-N,N')[[2,2'-sulfonylbis[acetato]](2-)-$0^1,0^1$]-platinum | 12.5 | 20.5 | 171 |
| | 6.2 | 23.5 | 196 |
| | 3.1 | 15 | 125 |
| | 1.5 | 12 | 100 |
| Control | — | 12 | — |
| Cisplatin | 2.5 | 16 | 133 |
| | 1.25 | 20.5 | 171 |
| Cis-(1,2-cyclohexanediamine-N,N')[pentanedioato(2-)-$0^1,0^5$] | 25 | 18.5 | 154 |
| | 12.5 | 15 | 125 |

TABLE I-continued

Lymphocytic Leukemia P388 Test

| Compound | Dose (mg/kg) | Median Survival (Days) | T/C × 100 (%) |
|---|---|---|---|
| platinum | 6.2 | 16 | 133 |
|  | 3.1 | 12.5 | 104 |
| Control | — | 12 | — |
| Cisplatin | 2.5 | 16 | 133 |
|  | 1.25 | 20.5 | 171 |
| Cis-(1,2-cyclohexanediamine-N,N')[[2,2'-sulfonylbis-[acetato]](2-)-O$^1$,O$^1$]platinum | 12.5 | 23 | 192 |
|  | 6.2 | 19 | 158 |
|  | 3.1 | 15 | 125 |
| Control | — | 12 | — |
| Cisplatin | 2.5 | 16 | 133 |
|  | 1.25 | 20.5 | 171 |
| Cis(and trans)-1,2-cylohexane-diamine, compound with [[2,2'-oxybis[acetato]](2-)-O$^1$,O$^1$]-platinum | 6 | 26.5 | 237 |
|  | 3 | 18.5 | 165 |
|  | 1.5 | 17.5 | 156 |
|  | 0.8 | 12 | 107 |
| Control | — | 11.2 | — |
| Cisplatin | 1 | 26.5 | 237 |
|  | 0.25 | 13.5 | 121 |
| (1R-trans-)1,2-cyclohexane-diamine, compound with [[2,2'-oxybis[acetato]](2-)-O$^1$,O$^1$]-platinum | 12 | 18.5 | 171 |
|  | 6 | 24 | 222 |
|  | 3 | 22 | 204 |
|  | 1.5 | 23 | 213 |
|  | 0.8 | 17 | 157 |
| Control | — | 10.8 | — |
| Cisplatin | 1 | 21.5 | 199 |
|  | 0.25 | 19.5 | 180 |
|  | 0.06 | 15.5 | 143 |

Melanotic Melanoma B16

The animals used were C57BC/6 mice, all of the same sex, weighing a minimum of 17 g and all within a 3 g weight range. There were 10 animals per test group. A 1 g portion of melanotic melanoma B$_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9, relative to tumor inoculation, at various doses. The animals were weighed and survivors recorded on a regular basis for 60 days. The median survival time for treated (T)/control (C) animals were calculated. The positive control compound was Cisplatin. The results of this test appear in Table II.

TABLE II

Melanotic Melanoma B16

| Compound | Dose (mg/kg) | Median Survival (Days) | T/C × 100 (%) |
|---|---|---|---|
| (2,2-dimethyl-1,3-propanedi-amine-N,N')[2,2'-oxybis-[acetato]](2-)O$^1$,O$^1$]platinum | 3 | 25.5 | 150 |
|  | 1.5 | 24.5 | 144 |
| Control | — | 17 | — |
| Cisplatin | 0.5 | 22.5 | 132 |
|  | 0.25 | 25 | 147 |
|  | 0.12 | 16 | 94 |
| Cis-(1,2-cyclohexanediamine-N,N')[[2,2'-oxybis[acetato]]-(2-)O$^1$,O$^1$]platinum | 3 | 25 | 139 |
|  | 1.5 | 26 | 144 |
|  | 0.8 | 23 | 128 |
|  | 0.4 | 22 | 122 |
| Control | — | 18 | — |
| Cisplatin | 0.4 | 28.5 | 158 |
|  | 0.2 | 24 | 133 |
|  | 0.1 | 22 | 122 |
|  | 0.05 | 22 | 122 |
| (1,1-cyclopentanedimethanamine-N,N')[[2,2'-oxybis-[acetato]]-(2-)-O$^1$,O$^1$]platinum | 3 | 21.5 | 116 |
|  | 1.5 | 30 | 162 |
|  | 0.8 | 28 | 151 |
|  | 0.4 | 24 | 130 |
| Control | — | 18.5 | — |
| Cisplatin | 0.4 | 22.5 | 122 |
|  | 0.2 | 21 | 114 |
|  | 0.1 | 19.5 | 105 |
|  | 0.05 | 20.5 | 111 |
| trans-(-)-(1,2-cyclohexanedi-amine-N,N')[[2,2'-sulfonylbis-[acetato]](2-)-O$^1$,O$^1$]platinum | 1.5 | 16 | 94 |
|  | 0.8 | 22 | 129 |
|  | 0.4 | 24.5 | 144 |
| Control | — | 17 | — |
| Cisplatin | 0.5 | 22.5 | 132 |
|  | 0.25 | 25 | 147 |
|  | 0.12 | 16 | 94 |
| (1,1-cyclobutanedimethanamine-N,N')[[2,2'oxybis[acetato]]-(2-)-O$^1$,O$^1$]platinum | 3 | 27 | 159 |
|  | 1.5 | 24.5 | 144 |
|  | 0.8 | 20.5 | 121 |
| Control | — | 17 | — |
| Cisplatin | 0.5 | 22.5 | 132 |
|  | 0.25 | 25 | 147 |
|  | 0.12 | 16 | 94 |
| (1,1-cyclohexanedimethanamine-N,N')[[2,2'-oxybis[acetato]]-(2-)-O$^1$,O$^1$]-platinum | 3 | 27.5 | 162 |
|  | 1.5 | 23 | 135 |
| Control | — | 17 | — |
| Cisplatin | 0.5 | 22.5 | 132 |
|  | 0.25 | 25 | 147 |
|  | 0.12 | 16 | 94 |
| trans-(racemic)-(1,2-cyclo-hexanediamine-N,N')[[2,2'-sulfonylbis[acetato]](2-)-O$^1$,O$^1$]platinum | 3 | 29.5 | 174 |
|  | 1.5 | 27.5 | 162 |
|  | 0.8 | 24 | 141 |
|  | 0.4 | 22 | 129 |
| Control | — | 17 | — |
| Cisplatin | 0.8 | 27.5 | 162 |
|  | 0.4 | 28 | 165 |
|  | 0.2 | 25 | 147 |
| Cis-(1,2-cyclohexanediamine-N,N')[[2,2'-sulfonybis-[acetato]](2-)-O$^1$,O$^1$]platinum | 6 | 24.5 | 144 |
|  | 3 | 23.5 | 138 |
|  | 1.5 | 24 | 141 |
|  | 0.8 | 21.5 | 126 |
|  | 0.4 | 19 | 112 |
| Control | — | 17 | — |
| Cisplatin | 0.8 | 27.5 | 162 |
|  | 0.4 | 28 | 165 |
|  | 0.2 | 25 | 147 |
| cis(and trans)-1,2-cyclohexane-diamine, compound with [[2,2'-oxybis[acetato]](2-)-O$^1$,O$^1$]-platinum | 1.5 | 29.5 | 180 |
|  | 0.8 | 27 | 165 |
|  | 0.4 | 23 | 140 |
|  | 0.2 | 19.5 | 119 |
| Control | — | 16.4 | — |
| Cisplatin | 0.4 | 26.5 | 162 |
|  | 0.2 | 23 | 140 |
|  | 0.1 | 21 | 128 |
| (1R-trans)-1,2-cyclohexanedi-amine compound with [[2,2'-oxybis[acetato]](2-)-O$^1$,O$^1$]-platinum | 0.8 | 33.5 | 186 |
|  | 0.4 | 27.5 | 153 |
|  | 0.2 | 25 | 139 |
|  | 0.1 | 22.5 | 125 |
| Control | — | 18 | — |
| Cisplatin | 0.4 | 25 | 139 |
|  | 0.1 | 21 | 125 |

Colon 26 Adenocarcinoma Test

The animals used were Balb/C mice all of one sex, weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. The test compounds were administered intraperitoneally on days 1, 5 and 9 (relative to tumor implant doses). The mice were weighed and deaths recorded on a regular basis for 30 days. The median survival times and the ratio of survival time for treated (T)/control (C) animals were calculated. The positive control compound was Cisplatin. The results of this test on representative compounds of this invention appear in Table III.

TABLE III

Colon 26 Adenocarcinoma

| Compound | Dose (mg/kg) | Median Survival (Days) | T/C × 100 (%) |
|---|---|---|---|
| trans-(racemic)-(1,2-cyclo-hexanediamine-N,N')[[2,2'-sulfonylbis[acetato]](2-)-$O^1,O^1$]platinum | 12 | 32.5 | 171 |
|  | 6 | 31 | 163 |
|  | 3 | 29 | 153 |
|  | 1.5 | 26.5 | 139 |
| Control | — | 19 | — |
| Cisplatin | 1 | 33 | 174 |
|  | 0.5 | 41.5 | 218 |
|  | 0.25 | 24.5 | 129 |
| cis-(1,2-cyclohexanediamine-N,N')[[2,2'-sulfonylbis[acetato]](2-)-$O^1,O^1$]platinum | 12.5 | 33 | 174 |
|  | 6 | 33 | 174 |
|  | 3 | 22 | 116 |
|  | 1.5 | 24 | 126 |
| Control | — | 19 | — |
| Cisplatin | 1 | 33 | 174 |
|  | 0.5 | 41.5 | 218 |
|  | 0.25 | 24.5 | 129 |
| (2,2-dimethyl-1,3-propanediamine-N,N')[[2,2'-oxybis[acetato]](2-)$O^1,O^1$]platinum | 3 | 21.5 | 130 |
| Control | — | 16.5 | — |
| Cisplatin | 1 | 23 | 139 |
|  | 0.5 | 15.5 | 94 |
|  | 0.25 | 17 | 103 |
| Cis(1,2-cyclohexanediamine-N,N')[[2,2'-oxybis[acetato]](2-)$O^1,O^1$]platinum | 12 | 29.5 | 159 |
|  | 6 | 31 | 168 |
|  | 3 | 28.5 | 154 |
|  | 1.5 | 23.5 | 127 |
| Control | — | 18.5 | — |
| Cisplatin | 1 | 29 | 157 |
|  | 0.5 | 34.5 | 186 |
|  | 0.25 | 24.5 | 132 |
|  | 0.125 | 22.5 | 122 |
| (1,1-cyclopentanedimethanamine-N,N'[[2,2'-oxybis[acetato]]-(2-)-$O^1,O^1$]platinum | 6 | 12 | 80 |
|  | 3 | 22 | 147 |
| Control | — | 15 | — |
| Cisplatin | 1 | 21.5 | 143 |
|  | 0.5 | 19 | 127 |
|  | 0.25 | 16.5 | 110 |
|  | 0.125 | 14.5 | 97 |
| trans-(-)-(1,2-cyclohexanediamine-N,N')[[2,2'-sulfonylbis[acetato]](2-)-$O^1,O^1$]platinum | 6 | 16 | 107 |
|  | 3 | 19.5 | 130 |
| Control | — | 15 | — |
| Cisplatin | 1 | 21.5 | 143 |
|  | 0.5 | 19 | 127 |
|  | 0.25 | 16.5 | 110 |
|  | 0.125 | 14.5 | 97 |
| (1,1-cyclobutanedimethanamine-N,N')-[[2,2'-oxybis[acetato]]-(2-)-$O^1,O^1$]platinum | 3 | 19 | 127 |
|  | 1.5 | 15 | 100 |
|  | 0.8 | 16 | 107 |
| Control | — | 15 | — |
| Cisplatin | 1 | 21.5 | 143 |
|  | 0.5 | 19 | 127 |
|  | 0.25 | 16.5 | 110 |
|  | 0.125 | 14.5 | 97 |
| (1,1-cyclohexanedimethanamine-N,N')[[2,2'-oxybis[acetato]]-(2-)-$O^1,O^1$]-platinum | 6 | 22 | 138 |
|  | 3 | 29.5 | 184 |
|  | 1.5 | 24.5 | 153 |
| Control | — | 16 | — |
| Cisplatin | 1 | 25 | 156 |
|  | 0.5 | 18 | 113 |
|  | 0.25 | 18 | 113 |
|  | 0.125 | 16 | 100 |
| cis(and trans)-1,2-cyclohexanediamine, compound with [[2,2'-oxybis[acetato]](2-)-$O^1,O^1$]-platinum | 6 | 29.5 | 159 |
|  | 3 | 24.5 | 132 |
| Control | — | 18.6 | — |
| Cisplatin | 0.5 | 38.5 | 207 |
|  | 0.25 | 37.5 | 201 |
| (1R-trans)-1,2-cyclohexanediamine, compound with [[2,2'-oxybis[acetato]](2-)-$O^1,O^1$]-platinum | 3 | 22 | 133 |
| Control | — | 16.5 | — |
| Cisplatin | 0.5 | 30.5 | 185 |
|  | 0.25 | 29.5 | 179 |

Lymphocytic Leukemia L1210 Test

The animals used were BDF$_1$ of CD$_2$F$_1$ mice, all of one sex, weighing a minimum of 17 g and all within a 3-g weight range. There were 6 mice in each test group and 18 in control groups. The tumor transplant was by intraperitoneal injection of 0.5 ml of lymphocytic leukemia L1210 at a concentration of 10$^5$ cells per mouse. The test compounds were administered on days 1, 5 and 9 (relative to tumor inoculation) at various doses. The mice were weighed and survivors recorded on a regular basis for 30 days. The median survival time and the ratio of survival time for treated (T)/control (C) animals were calculated. The positive control compound was Cisplatin given intraperitoneally at the indicated doses. The results of this test on representative compounds of this invention appear in Table IV.

TABLE IV

Lymphocytic Leukemia L1210

| Compound | Dose (mg/kg) | Median Survival (Days) | T/C × 100 (%) |
|---|---|---|---|
| (2,2-dimethyl-1,3-propanediamine-N,N')[[2,2'oxybis[acetato]](2-)$O^1,O^1$]platinum | 6 | 19 | 211 |
|  | 3.1 | 15.5 | 172 |
|  | 1.5 | 12.5 | 139 |
| Control | — | 9 | — |
| Cisplatin | 5 | 15 | 167 |
|  | 2.5 | 13 | 144 |
|  | 1.25 | 9.5 | 106 |
| (1,1-cyclopentanedimethanamine-N,N')[[2,2'-oxybis[acetato]]-(2-)-$O^1,O^1$]platinum | 6 | 23 | 267 |
|  | 3 | 10.2 | 119 |
|  | 1.5 | 12.6 | 147 |
| Control | — | 8.6 | — |
| Cisplatin | 5 | 18.7 | 217 |
|  | 2.5 | 13.3 | 155 |
|  | 1.25 | 10 | 116 |
| trans-(-)-(1,2-cyclohexanediamine-N,N')[[2,2'-sulfonylbis[acetato]](2-)-$O^1,O^1$]platinum | 25 | 13 | 151 |
|  | 12.5 | 21.3 | 248 |
|  | 6.2 | 23.5 | 273 |
| Control | — | 8.6 | — |
| Cisplatin | 5 | 18.7 | 217 |
|  | 2.5 | 13.3 | 155 |
|  | 1.25 | 10 | 116 |
| trans-(racemic)-(1,2-cyclohexanediamine-N,N')[[2,2'-sulfonylbis[acetato]](2-)-$O^1,O^1$]platinum | 12.5 | >30 | >375 |
|  | 6.2 | 13.5 | 169 |
|  | 3.1 | 11 | 138 |
|  | 1.5 | 9 | 113 |
| Control | — | 8 | — |
| Cisplatin | 2.5 | 14 | 175 |
| cis-(1,2-cyclohexanediamine-N,N')[[2,2'-sulfonylbis[acetato]](2-)-$O^1,O^1$]platinum | 12.5 | 12.5 | 156 |
|  | 6.2 | 9 | 113 |
|  | 3.1 | 9.5 | 119 |
|  | 1.5 | 8.5 | 106 |
| Control | — | 14 | — |
| Cisplatin | 2.5 | 14 | 175 |
| (1,1-cyclobutanedimethanamine-N,N')[[2,2'-oxybis[acetato]]-(2-)-$O^1,O^1$]platinum | 6.2 | 18 | 200 |
|  | 3.1 | 13 | 144 |
|  | 1.5 | 10 | 111 |
|  | 0.8 | 9 | 100 |
| Control | — | 9 | — |
| Cisplatin | 5 | 19 | 211 |
|  | 2.5 | 13.5 | 150 |
|  | 1.25 | 10 | 111 |
| (1,1-cyclohexanedimethanamine-N,N')[[2,2'-oxybis[acetato]]-(2-)-$O^1,O^1$]platinum | 6.2 | 15 | 167 |
|  | 3.1 | 13.5 | 150 |
|  | 1.5 | 11 | 122 |
| Control | — | 9 | — |
| Cisplatin | 5 | 19 | 211 |
|  | 2.5 | 13.5 | 150 |
|  | 1.25 | 10 | 111 |

TABLE IV-continued

Lymphocytic Leukemia L1210

| Compound | Dose (mg/kg) | Median Survival (Days) | T/C × 100 (%) |
|---|---|---|---|
| Cis(and trans)-1,2-cylohexane-diamine, compound with [[2,2'-oxybis[acetato]](2-)-0¹,0¹]-platinum | 12.5 | 16.6 | 161 |
| Control | — | 10.3 | — |
| (1R-trans)-1,2-cyclohexane-diamine, compound with [[2,2'-oxybis[acetato]](2-)-0¹,0¹]-platinum | 12 | 25 | 281 |
| | 6 | 25.4 | 285 |
| | 3 | 13.8 | 155 |
| | 1.5 | 11.8 | 133 |
| Control | — | 8.9 | — |
| Cisplatin | 6 | 18.7 | 207 |
| | 3 | 14.6 | 164 |
| | 1.5 | 11.4 | 128 |

M5076 Sarcoma

The M5076 reticular cell sarcoma is propagated as subcutaneous (sc) implants in C57B2/6 female mice. In the assays for antitumor activity, BDF₁ mice of either sex were inoculated intraperitoneally (ip) with 0.5 ml of a 10% tumor brei. Test compounds were administered ip on days 1, 5, 9, 13 and 17 relative to tumor inoculation on day zero. The median survival time in days was determined for each drug dose used on day 60 and the ratio of survival time for treated (T)/control (C) animals were calculated.

The results of this test on representative compounds of this invention appear in Table V, compared to the results obtained with Cisplatin.

TABLE V

M5076 Sarcoma Test

| Compound | Dose (mg/kg) | Median Survival (Days) | T/C × 100 (%) |
|---|---|---|---|
| trans-(racemic)-(1,2-cyclo-hexanediamine-N,N')[[2,2'-sulfonylbis[acetato]](2-)-0¹,0¹]platinum | 6 | >60 | >207 |
| | 3 | >60 | >207 |
| | 1.5 | >60 | >207 |
| Control | — | 29 | — |
| Cisplatin | 1.6 | 50.5 | 174 |
| | 0.8 | 44 | 152 |
| cis-(1,2-cyclohexandiamine-N,N')[[2,2'-sulfonylbis-[acetato]](2-)-0¹,0¹]platinum | 12.5 | >60 | >207 |
| | 6 | >60 | >207 |
| | 3 | 56 | 193 |
| | 1.5 | >60 | >207 |
| Control | — | 29 | — |
| Cisplatin | 1.6 | 50.5 | 174 |
| | 0.8 | 44 | 152 |
| (2,2-dimethyl-1,3-propanedi-amine-N,N')[[2,2'-oxybis-[acetato]](2-)0¹,0¹]platinum | 3 | >60 | >194 |
| | 1.5 | 55 | 177 |
| | 0.8 | 57 | 184 |
| | 0.4 | 51 | 165 |
| Control | — | 31 | — |
| Cisplatin | 1.6 | 50 | 161 |
| | 0.8 | 43 | 139 |
| Cis-(1,2-cyclohexanediamine-N,N')[[2,2'-oxybis[acetato]]-(2-)-0¹,0¹]platinum | 6 | >60 | >207 |
| | 3 | >60 | >207 |
| | 1.5 | >60 | >207 |
| Control | — | 29 | — |
| Cisplatin | 1.6 | >60 | >207 |
| | 0.8 | 56 | 193 |
| (1,1-cyclopentanedimethanamine-N,N')[2,2'-oxybis[acetato]](2-)-0¹,0¹]platinum | 3 | >60 | >250 |
| | 1.5 | >60 | >250 |
| | 0.8 | 46 | 192 |
| Control | — | 24 | — |
| Cisplatin | 1.6 | 53.5 | 223 |
| | 0.8 | 47 | 196 |
| trans-(-)-(1,2-cyclohexanedi-amine-N,N')[[2,2'-sulfonylbis-[acetato]](2-)-0¹,0¹]platinum | 6 | >57 | >184 |
| | 3 | >60 | >194 |
| | 1.5 | >60 | >194 |
| | 0.8 | >60 | >194 |
| Control | — | 31 | — |

TABLE V-continued

M5076 Sarcoma Test

| Compound | Dose (mg/kg) | Median Survival (Days) | T/C × 100 (%) |
|---|---|---|---|
| Cisplatin | 1.6 | 50 | 161 |
| | 0.8 | 43 | 139 |
| (1,1-cyclobutanedimethanamine-N,N')[[2,2'-oxybis[acetato]]-(2-)-0¹,0¹]platinum | 3 | >60 | >194 |
| | 1.5 | >60 | >194 |
| | 0.8 | >60 | >194 |
| | 0.4 | 34.5 | 111 |
| Control | — | 31 | — |
| Cisplatin | 1.6 | 50 | 161 |
| | 0.8 | 43 | 139 |
| (1,1-cylohexanedimethanamine-N,N')[2,2'-oxybis[acetato]]-(2-)-0¹,0¹]platinum | 6 | >60 | >194 |
| | 3 | >60 | >194 |
| | 1.5 | >60 | >194 |
| | 0.8 | 53.5 | 173 |
| Control | — | 31 | — |
| Cisplatin | 1.6 | 50 | 161 |
| | 0.8 | 43 | 139 |
| Cis(and trans)1,2-cyclohexane-diamine, compound with [[2,2'-oxybis[acetato]](2-)-0¹,0¹]-platinum | 6 | >60 | >252 |
| | 3 | >60 | >252 |
| | 1.5 | >60 | >252 |
| | 0.8 | >60 | >252 |
| Control | — | 23.8 | — |
| Cisplatin | 1 | >60 | >252 |
| | 0.5 | 51.5 | 216 |
| (1R-trans)-1,2-cyclohexane-diamine, compound with [[2,2'-oxybis[acetato]](2-)-0¹,0¹]-platinum | 3 | >60 | >252 |
| | 1.5 | >60 | >252 |
| | 0.8 | >60 | >252 |
| Control | — | 23.8 | — |
| Cisplatin | 1 | >60 | >252 |
| | 0.5 | 51.5 | 216 |

Another aspect of the invention comprises novel compositions of matter and the method of inducing the regression and/or palliation of leukemia and other cancers in mammals using the novel compounds of this invention when administered in amounts ranging from about 1 mg to about 1.2 g per square meter of body surface area per day. The interrelationship of dosages for animals of various sizes and species and humans (based on mg/m² of surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219–244, May 1966. A preferred dosage regimen for optimum results would be from about 3 mg/m²/day to about 200 mg/m²/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion median containing, for example, water, ethanol, polyol (e.g. glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferably to include isotonic agents, for example, sugars or sodium chloride. Prolonged absorption of the injectable compositions can be obtained by the use in the compositions of agents which delay absorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate of less frequent days. As can be seen from the dosage regimens, the amount of principal active ingredient administered is a sufficient amount to aid regression and palliation of leukemia and other cancers, in the absence of excessive deleterious side effects of a cytotoxic nature to the host harboring the cancer. As used herein, cancer disease means blood malignancies such as leukemia, and other solid and non-solid malignancies such as the melanomas adenocarcinomas and sarcomas. By regression and palliation is meant arresting or retarding the growth of the tumor or other manifestation of the disease compared to the course of the disease in the absence of treatment.

This invention will be described in greater detail in conjunction with the following non-limiting specific examples.

EXAMPLE 1

Cis(and trans)-1,2-cyclohexanediamine, compound with [[2,2'-oxybis[acetato]](2-)-$O^1,O^1$]platinum To a solution of 4.56 g of 1,2-diaminocyclohexane in 20 ml of water was added a solution of 16.6 g of potassium tetrachloroplatinate in 100 ml of water. The resulting suspension was stirred overnight, then the yellow solid was collected, washed with water and dried, giving 15 g of 1,2-cyclohexanediamine, compound with platinum chloride.

A 2.05 g portion of 98% diglycolic acid was dissolved in a mixture of 10 ml of water and 3 ml of 10N sodium hydroxide. To this was added a solution of 5.09 g of silver nitrate in 20 ml of water. The resulting suspension was stirred overnight, then the solid was collected, washed with water and dried, giving 4.96 g of 2,2'-oxybisacetic acid, disilver salt.

A suspension of 1.91 g of 1,2-cyclohexanediamine, compound with platinum chloride, 1.73 g of 2,2'-oxybisacetic acid, disilver salt and 200 ml of water was stirred in the dark overnight. The solid was removed by filtration and the filtrate evaporated to dryness, giving 1.59 g of the desired product, mp 225° C. (dec.).

EXAMPLE 2

(1R-trans)-1,2-Cyclohexanediamine, compound with [[2,2'-oxybis[acetato]](2-)-$O^1,O^1$]platinum A 4.56 g portion of trans-1,2-diaminocyclohexane was dissolved in 20 ml of water. To this was added a solution of 16.6 g of potassium tetrachlorplatinate in 100 ml of water. The resulting suspension was stirred for 3.5 hours, then the solid was collected, washed with water and dried, giving 14.28 g of trans-1,2-cyclohexanediamine, compound with platinum chloride.

A suspension of 1.14 g of the above platinum derivative, 1.043 g of 2,2'-oxybisacetic acid, disilver salt and 100 ml of water was stirred overnight, then filtered and the filtrate evaporated to dryness, giving 677 mg of the desired product, mp 232° C. (dec).

EXAMPLE 3

(2,2-Dimethyl-1,3-propanediamineN,N')-[[2,2'-oxybis-[acetato]](2-)-O$^1$,O$^1$]platinum To a solution of 12.45 g of potassium tetrachloroplatinate in 60 ml of water was added 3.06 g of 2,2-dimethyl-1,3-propanediamine. The mixture was allowed to stand overnight, giving 7.0 g of 2,2-dimethyl-1,3-propanediamine, compound with platinum chloride.

A suspension of 1.105 g of the above platinum derivative, 1.04 g of 2,2'-oxybisacetic acid, disilver salt and 100 ml of water was stirred in the dark overnight and then filtered. The filtrate was evaporated to dryness, giving 908 mg of the desired product, mp 205° C. (dec).

EXAMPLE 4 trans-(racemic)-(1,2-Cyclohexanediamine-N,N')[[2,2'-oxybis[acetato]](2-)-O$^1$,O$^1$]platinum A solution of 33.2 g of potassium tetrachloroplatinate in 200 ml of water was added to a solution of 9.12 g of dl-trans-1,2-diaminocyclohexane in 40 ml of water. The resulting suspension was stirred for 3.5 hours, then the solid was collected, washed with water and dried, giving 26.7 g of trans-(racemic)-1,2-cyclohexanediamine, compound with platinum chloride.

A suspension of 1.91 g of the above platinum derivative, 1.73 g of 2,2'-oxybisacetic acid, disilver salt and 200 ml of water was stirred in the dark overnight and then filtered. The filtrate was evaporated to dryness, the residue slurried in methanol and diluted with ether. The solid was collected, giving 1.54 g of the desired product, mp 227° C. (dec).

EXAMPLE 5

Cis-(1,2-Cyclohexanediamine-N,N')-[[2,2'-oxybis-[acetato]](2-)-O$^1$,O$^1$]platinum A solution of 11.07 g of potassium tetrachloroplatinate in 60 ml of water was added to a solution of 3.04 g of cis-1,2-diaminocyclohexane in 20 ml of water. The resulting suspension was stirred for 3.5 hours, then the solid was collected, washed with water and dried, giving 8.74 g of cis-1,2-cyclohexanediamine, compound with platinum chloride.

A suspension of 1.8 g of the above platinum derivative, 1.65 g of 2,2'-oxybisacetic acid, disilver salt and 200 ml of water was stirred in the dark overnight and then filtered. The filtrate was evaporated to dryness, the residue slurried in methanol, diluted with ether and filtered, giving 981 mg of the desired product, mp 220° C. (dec).

EXAMPLE 6

Diamine[[2,2'-oxybis[acetato]](2-)-O$^1$,O$^1$]platinum

A suspension of 1.2 g of cisplatin, 1.39 g of 2,2'-oxybisacetic acid, disilver salt and 100 ml of water was stirred overnight in the dark and then filtered. The filtrate was evaporated to dryness, giving 1.29 g of the desired product, mp 190° C. (dec).

EXAMPLE 7

(1,1-Cyclopentanedimethanamine-N,N')-[[2,2'-oxybis-[acetato]](2-)-O$^1$,O$^1$]platinum A mixture of 43.19 g of 1,4-dibromobutane, 13.2 g of malononitrile, 55.3 g of potassium carbonate and 1 liter of acetonitrile was refluxed for 42 hours, filtered while hot and evaporated to dryness giving a dark oil. This oil was vacuum distilled, giving 12.8 g 1,1-cyclopentanedicarbonitrile.

A 12.0 g portion of the above compound in 150 ml of tetrahydrofuran was treated dropwise with 300 ml of 1N borane in tetrahydrofuran over 1 hour. The mixture was then stirred for 0.5 hour, refluxed for 5 hours, cooled to room temperature and treated dropwise with 50 ml methanol. The mixture was stirred overnight, then cooled to −10° C. and dry hydrogen chloride gas bubbled in until the pH reached 2.0. The mixture was then refluxed for 2 hours, cooled and evaporated. The residue was taken up in methanol and evaporated three times giving 18.2 g of 1,1-cyclopentanedimethanamine, dihydrochloride.

A 2.01 g portion of this amine derivative was dissolved in 20 ml of 1N sodium hydroxide, the pH was adjusted to 7.0 with hydrochloric acid and 4.15 g of potassium tetrachloroplatinate was added. The mixture was stirred for 4 hours, then the solid was collected, washed with water and dried, giving 2.1 g of 1,1-cyclopentanedimethanamine, compound with platinum chloride.

A solution of 1.36 g of silver nitrate in 15 ml of water was added to a suspension of 1.577 g of the above platinum derivative in 10 ml of water. This mixture was stirred in the dark for 3.5 hours and then filtered. To the filtrate was added a solution of 547 mg of 98% diglycolic acid in 8 ml of 1N sodium hydroxide. This solution was stirred for 2 hours, then concentrated to about 15 ml, giving 667 mg of the desired product, mp 250° C. (dec.).

EXAMPLE 8

Bis-(2-methylpropanamine)[[2,2'-oxybis-[acetato]](2-)-O$^1$,O$^1$]platinum

A mixture of 2.926 g of isobutylamine, 8.3 g of potassium tetrachloroplatinate and 50 ml of water was stirred for 3 hours, then the solid was collected, washed with water and dried, giving 5.98 g of dischlorobis(2-methyl-1-propanamine)platinum.

A solution of 1.69 g of silver nitrate in 15 ml of water was added to a suspension of 2.08 g of the above platinum derivative in 15 ml of water. This mixture was stirred in the dark for 4 hours and then filtered. To the filtrate was added a solution of 720 mg of 98% diglycolic acid in 5 ml of water and 10 ml of 1N sodium hydroxide. This suspension was stirred overnight, the solid collected, washed with water and dried, giving 1.29 g of the desired product, 150° C. (dec.).

EXAMPLE 9 trans-(-)-(1,2-Cyclohexanediamine-N,N')-[[2,2'-sulfonylbis[acetato]](2-)-O$^1$,O$^1$]platinum To a mixture of 50 ml of 30% hydrogen peroxide and 200 ml of acetic acid at 80° C. was added, in portions, 30 g of thiodiglycolic acid. The solution was heated at 80° C. for 2 hours, then evaporated and the residue recrystallized from ethanol-ether, giving 4.2 g of sulfonyldiacetic acid.

A 1.9 g portion of trans-1,2-cyclohexanediamine, compound with platinum chloride was added to a solution of 1.69 g of silver nitrate in 30 ml of water. This suspension was stirred in the dark for 3 hours, then filtered. To the filtrate was added a solution of 911 mg of sulfonyldiacetic acid in 10 ml of 1N sodium hydroxide. The mixture was stirred in the dark overnight and the solid collected, washed with water and dried, giving 1.73 g of the desired product, mp >200° C. (dec.).

EXAMPLE 10

(1,1-Cyclobutanedimethanamine-N,N')-[[2,2'-oxybis[acetato]](2-)-O¹,O¹]platinum

A mixture of 10 g of 1,3-dibromopropane, 3.30 g of malononitrile, 13.8 g of potassium carbonate and 200 ml of acetonitrile was refluxed on a steam bath for 3 hours, then filtered while hot. The filtrate was concentrated to an oil which was taken up in dichloromethane, extracted three times with water, dried and concentrated to an oil. This oil was vacuum distilled, giving at 41°–44° C., 0.4 mm, 1,1-cyclobutanedicarbonitrile.

A 10.6 g portion of 1,1-cyclobutane dicarbonitrile in 150 ml of tetrahydrofuran was treated dropwise over 1 hour with 300 ml of 1N borane in tetrahydrofuran in an ice bath. The mixture was then stirred for 20 hours at room temperature, 125 ml of ethanol was added dropwise, the mixture stirred for 12 hours, filtered and concentrated to dryness. The residue was treated with 100 ml of water, basified with 6N sodium hydroxide, extracted with dichloromethane, dried and evaporated. The residue was taken up in ether, treated with 33 ml of 6N hydrochloric acid in isopropanol. The solid was collected and recrystallized from methanol, giving 2.74 g of 1,1-cyclobutanedimethanamine, dihydrochloride.

A solution of 1.87 g of the above amine in 30 ml of water was treated with 1.64 g of solid sodium acetate followed by 4.15 g of potassium tetrachloroplatinate. The mixture was stirred overnight and filtered. The filtrate was concentrated, giving as a solid 1,1-cyclobutanedimethanamine, compound with platinum chloride.

A 0.7 g portion of the above platinum derivative was reacted with silver nitrate and diglycolic acid as described in Example 8, giving 470 mg of the desired product, mp 211°–212° C.

EXAMPLE 11

(1,1-Cyclohexanedimethanamine-N,N')-[[2,2'-oxybis[acetato]](2-)-O¹,O¹]platinum 1,1-Cyclohexanedicarbonitrile was prepared from 1,5-dibromopropane and malononitrile as described in Example 10.

The above carbonitrile was converted to 1,1-cyclohexanedimethanamine, dihydrochloride and then to 1,1-cyclohexanedimethanamine, compound with platinum chloride, essentially by the procedure of Example 10.

This platinum derivative was then treated with silver nitrate and diglycolic acid as described in Example 10, giving 700 mg of the desired product, mp 220°–222° C.

EXAMPLE 12

Diamine[[2,2'-sulfonylbis[acetato]]-(2-)-O¹,O¹]platinum

A 3.0 g portion of sulfonyldiacetic acid was dissolved in a mixture of 6.55 ml of 5N sodium hydroxide and 10 ml of water. A solution of 5.59 g of silver nitrate in 16 ml of water was added and the suspension was stirred in the dark overnight. The solid was collected, washed with water and dried, giving 5.3 g of 2,2'-sulfonylbisacetic acid, disilver salt.

A suspension of 1.58 g of the above silver salt and 1.2 g of cisplatin in 200 ml of water was stirred in the dark overnight and then filtered. The filtrate was evaporated to dryness, giving 564 mg of the desired product, mp >200° C. (dec.).

EXAMPLE 13 trans-(racemic)-(1,2-Cyclohexanediamine-N,N')-[[2,2'-sulfonylbis[acetato]](2-)-O¹,O¹]platinum A suspension of 1.08 g of trans-(racemic)-1,2-cyclohexanediamine, compound with platinum chloride, 1.12 g of 2,2'-sulfonylbisacetic acid, disilver salt and 150 ml of water was stirred in the dark overnight and then filtered. The filtrate was evaporated to dryness, giving 984 mg of the desired product, mp >240° C. (dec.).

EXAMPLE 14

Cis-(1,2-Cyclohexanediamine-N,N')-[pentanedioato(2-)-O¹,O⁵]platinum

An 11.76 g portion of 97% glutaric anhydride was dissolved in a mixture of 40 ml of 5N sodium hydroxide and 200 ml of water. A solution of 33.8 g of silver nitrate in 100 ml of water was added, the suspension was stirred for 1 hour in the dark, then the solid was collected, washed with water and dried, giving 33.5 g of glutaric acid, disilver salt.

A suspension of 1.04 g of the glutaric acid, disilver salt, 1.14 g of cis-1,2-cyclohexanediamine, compound with platinum chloride and 150 ml of water was stirred in the dark overnight and then filtered. The filtrate was evaporated, giving 541 mg of the desired product, mp 212° C. (dec.).

EXAMPLE 15

Cis-(1,2-Cyclohexanediamine-N,N')-[[2,2'-sulfonylbis[acetato]](2-)-O¹,O¹]platinum A solution of 1.8 g of silver nitrate in 5 ml of water was added to a suspension of cis-1,2-cyclohexanediamine, compound with platinum chloride in 25 ml of water and this was stirred in the dark for 3.5 hours and then filtered. To the filtrate was added a solution of 965 mg of sulfonyldiacetic acid in 10.6 ml of 1N sodium hydroxide. The mixture was allowed to stand 2 hours and was then filtered. The filtrate was stored overnight and the solid collected, giving 650 mg of the desired product, mp >230° C. (dec.).

EXAMPLE 16 trans-(racemic)-(1,2-Cyclohexanediamine-N,N')-[pentanedioato(2-)-O¹,O⁵]platinum

A suspension of 1.14 g of trans-(racemic)-1,2-cyclohexanediamine, compound with platinum chloride, 1.04 g of glutaric acid disilver salt and 150 ml of water was stirred in the dark overnight and then filtered. The filtrate was evaporated to dryness, giving 1.23 g of the desired product, mp 224° C. (dec.).

We claim:

1. A compound selected from those of the formula:

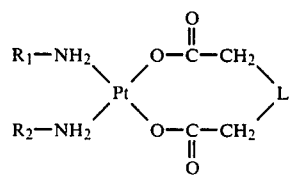

where $R_1$ and $R_2$ are individually selected from the group consisting of hydrogen and alkyl($C_1$-$C_6$); or $R_1$ and $R_2$ taken together are selected from the group consisting of $$(CH_2)_n \begin{array}{c} CH- \\ | \\ CH- \end{array}$$

where n is an integer 3-6, $$(CH_2)_m \begin{array}{c} CH_2- \\ C \\ CH_2- \end{array}$$

where m is an integer 3-6, and $$\begin{array}{c} -CH_2 \\ \phantom{-}C(CH_3)_2; \\ -CH_2 \end{array}$$

and L is selected from the group consisting of —O—, $$\begin{array}{c} O\diagdown\!\!\diagup O \\ -S- \end{array}, \quad N-\overset{O}{\overset{\|}{C}}-R_3 \text{ and } \diagup\!\!\!\diagdown NR_3$$

where $R_3$ is alkyl($C_1$-$C_6$) or —$CH_2CH_2OH$.

2. The compound according to claim 1, cis-(and trans)-1,2-cyclohexanediamine, compound with [[2,2'-oxybis[acetato]](2-)-$O^1,O^1$]platinum.

3. The compound according to claim 1, (1R-trans)-1,2-cyclohexanediamine, compound with [2,2'-oxybis[acetato]](2-)-$O^1,O^1$]platinum.

4. The compound according to claim 1, (2,2-dimethyl-1,3-propanediamine-N,N')[[2,2'-oxybis[acetato]]-(2-)-$O^1,O^1$]platinum.

5. The compound according to claim 1, trans(-racemic)-(1,2-cyclohexandeiamine, N,N',)[[2,2'-oxybis[acetato]](2-)-$O^1,O^1$]platinum.

6. The compound according to claim 1, cis-(1,2-cyclohexanediamine-N,N',)[[2,2'-oxybis[acetato]]-$O^1,O^1$]platinum.

7. The compound according to claim 1, (1,1-cyclopentanedimethanamine, N,N')[[2,2'-oxybis[acetato]](2-)-$O^1,O^1$]platinum.

8. The compound according to claim 1, bis-(2-methylpropanamine)[[2,2'-oxybis[acetato]](2-)-$O^1,O^1$]-platinum.

9. The compound according to claim 1, trans)-(-)-(1,2-cyclohexanediamine, N,N')-[[2,2'-sulfonylbis-[acetato]](2-)-$O^1,O^1$]platinum.

10. The compound according to claim 1, (1,1-cyclobutanedimethanamine-N,N'),[[2,2'-oxybis[acetato]](2-)-$O^1,O^1$]platinum.

11. The compound according to claim 1, (1,1-cyclohexanedimethanamine-N,N',)[[2,2'-oxybis-[acetato]](2-)-$O^1,O^1$]platinum.

12. The compound according to claim 1, diammine[[2,2'-sulfonylbis[acetato]](2-)-$O^1,O^1$]platinum.

13. The compound according to claim 1, trans(-racemic)-(1,2-cyclohexanediamine-N,N',)[[2,2'-sulfonylbis[acetato]](2-)-$O^1,O^1$]platinum.

14. The compound according to claim 1, cis-(1,2-cyclohexanediamine-N,N',)[[2,2'-sulfonylbis-[acetato]](2-)-$O^1,O^1$]platinum.

15. A composition of matter in dosage unit form comprising from about 1 mg to about 1.2 g per square meter of mammalian body surface area of a compound of claim 1, in association with a pharmaceutically acceptable carrier.

16. A compound selected from those of the formula:

$$\begin{array}{c} R_1-NH_2 \diagdown \phantom{Pt} \diagup \overset{O}{\overset{\|}{P-C}}-CH_2 \diagdown \\ \phantom{R_1-NH_2 \diagdown} Pt \phantom{\diagup \overset{O}{\overset{\|}{P-C}}-CH_2} L \\ R_1-NH_2 \diagup \phantom{Pt} \diagdown O-\underset{\|}{\underset{O}{C}}-CH_2 \diagup \end{array}$$

where $R^1$ and $R_2$ are individually selected from the group consisting of hydrogen and alkyl($C_1$-$C_6$); or $R_1$ and $R_2$ taken together are selected from the group consisting of $$(CH_2)_m \begin{array}{c} CH- \\ | \\ CH- \end{array}$$

where n is an integer 3-6, $$(CH_2)_m \begin{array}{c} CH_2- \\ C \\ CH_2- \end{array}$$

where m is an integer 3-6, and $$\begin{array}{c} -CH_2 \\ \phantom{-}C(CH_3)_2; \\ -CH_2 \end{array}$$

and L is selected from the group consisting of —O—, $$\begin{array}{c} O\diagdown\!\!\diagup O \\ -S- \end{array}, \text{ and } \diagup N-\overset{O}{\overset{\|}{C}}-R_3.$$

17. A composition of matter in dosage unit form comprising from about 1 mg to about 1.2 g per square meter of mammalian body surface area of a compound of claim 16, in association with a pharmaceutically acceptable carrier.

* * * * *